(12) United States Patent
Miracle et al.

(10) Patent No.: US 6,610,646 B2
(45) Date of Patent: Aug. 26, 2003

(54) ENHANCED DURATION FRAGRANCE DELIVERY SYSTEM HAVING A NON-DISTORTED INITIAL FRAGRANCE IMPRESSION

(75) Inventors: Gregory Scot Miracle, Hamilton, OH (US); Robert Richard Dykstra, Cleves, OH (US); Lynette Anne Makins Holland, Watford (GB); Jill Maureen Mattila, Chalfont St. Peter (GB)

(73) Assignee: The Procter & Gamble Company, Cincinnati, OH (US)

( * ) Notice: Subject to any disclaimer, the term of this patent is extended or adjusted under 35 U.S.C. 154(b) by 290 days.

(21) Appl. No.: 09/870,273

(22) Filed: May 30, 2001

(65) Prior Publication Data

US 2002/0049150 A1 Apr. 25, 2002

Related U.S. Application Data

(60) Provisional application No. 60/208,466, filed on Jun. 1, 2000.

(51) Int. Cl.$^7$ ................................................. A61K 7/46
(52) U.S. Cl. .................... 512/1; 512/2; 512/3; 510/101
(58) Field of Search ...................... 512/1, 2, 3; 510/101

(56) References Cited

U.S. PATENT DOCUMENTS

| | | |
|---|---|---|
| 5,559,088 A | 9/1996 | Severns et al. |
| 5,562,847 A | 10/1996 | Waite et al. |
| 5,652,205 A | 7/1997 | Hartman |
| 5,710,122 A | 1/1998 | Sivik et al. |
| 5,716,918 A | 2/1998 | Sivik et al. |
| 5,721,202 A | 2/1998 | Waite et al. |
| 5,744,435 A | 4/1998 | Hartman et al. |
| 5,756,827 A | 5/1998 | Sivik et al. |
| 5,919,752 A | 7/1999 | Moreli et al. |
| 5,965,767 A | 10/1999 | Sivik et al. |
| 6,013,618 A | 1/2000 | Morelli et al. |
| 6,077,821 A | 6/2000 | Morelli et al. |
| 6,083,892 A | 7/2000 | Severns et al. |
| 6,087,322 A | 7/2000 | Morelli et al. |
| 6,093,691 A | 7/2000 | Sivik et al. |
| 6,100,233 A | 8/2000 | Sivik et al. |
| 6,114,302 A | 9/2000 | Morelli et al. |
| 6,126,953 A | 10/2000 | Costa et al. |
| 6,147,037 A | 11/2000 | Gardlik et al. |
| 6,150,310 A | 11/2000 | Sivik et al. |
| 6,156,710 A | 12/2000 | Sivik et al. |
| 6,165,953 A | 12/2000 | Gardlik et al. |
| 6,177,389 B1 | 1/2001 | Morelli et al. |
| 6,184,188 B1 | 2/2001 | Severns et al. |

FOREIGN PATENT DOCUMENTS

| | | |
|---|---|---|
| WO | WO 97/34578 A1 | 9/1997 |
| WO | WO 99/43667 A1 | 9/1999 |
| WO | WO 00/24721 A1 | 5/2000 |

*Primary Examiner*—Jill Warden
*Assistant Examiner*—Monique T. Cole
(74) *Attorney, Agent, or Firm*—Richard S. Echler, Sr.

(57) ABSTRACT

The present invention relates to sustained release fragrance accords wherein the initial fragrance release or bouquet is not distorted by the presence of an unbalanced accord. The systems of the present invention comprise:

a) a pro-fragrance component; and b) a free fragrance component.

The present invention further relates to compositions comprising the fragrance raw materials systems and processes for preparing said systems.

34 Claims, No Drawings

ENHANCED DURATION FRAGRANCE DELIVERY SYSTEM HAVING A NON-DISTORTED INITIAL FRAGRANCE IMPRESSION

This Application claims priority to U.S. Provisional Patent Application Serial No. 60/208,466 filed Jun. 1, 2000.

FIELD OF THE INVENTION

The present invention relates to sustained release fragrance accords wherein the initial fragrance release or bouquet is not distorted by the presence of an unbalanced accord. The systems of the present invention comprise fragrance raw materials and one or more pro-fragrances and/or pro-accords which provide enhanced longevity of the initial fragrance accords.

BACKGROUND OF THE INVENTION

The art relating to pro-accords and pro-fragrances has recently been advanced to the point where a single molecule is capable of releasing a mixture of fragrance raw materials. By manipulation of the pro-accord or pro-fragrance structure, inter alia, acetal, ketal, orthoester, the formulator is now capable of delivering any class of fragrance raw material, inter alia, aldehydes, ketones, alcohols. In addition, by selecting the secondary structure of the pro-accord or pro-fragrance, the formulator can control the rate of fragrance release and the conditions under which said release will be sustained.

The initial impression imparted by fully formulated fragrances and accords is an important aesthetic attribute and provides the user with a display of the fragrance which will be imparted to others as they come into contact with the user. This initial impression is typically delivered to a situs, inter alia, skin which frequently has no other scents or fragrances to interfere with the character of the accord.

However, due to differential evaporation of the various perfume components, fully formulated fragrances (accords) have an initial fragrance profile which is different from the fragrance profile once the perfume top notes have begun to evaporate. The deliberate replenishment of these depleted top notes, together with any depleted lesser volatile middle and base notes, by pro-fragrances and pro-accords provides a first step in ameliorating the gradual change over time of the initial fragrance profile. However, use of pro-fragrances and pro-accords can contribute, in combination with free fragrance raw materials, to a distorted initial fragrance impression.

There exists no method or system by which the formulator can overcome this initial fragrance distortion. There is a long felt need for a process and a means for determining in which quantities fragrance raw materials, inter alia, initial fragrances or accords, and the pro-fragrances or pro-accords from which these components are released need to be admixed to supply a non-distorted initial fragrance impression. There is also no fragrance delivery system which allows the formulator to deliver a perfume accord which is balanced at the time of application and remains so over an extended period of time.

SUMMARY OF THE INVENTION

The present invention meets the aforementioned needs in that a fragrance delivery system and a method for determining the relative concentrations of ingredients necessary to provide both a balanced initial and sustained accord impression has been surprisingly discovered. By employing the steps described herein the formulation of balanced delivery systems can now be accomplished. The formulator can now employ any number of pro-accords or pro-fragrances to deliver a sustained fragrance character or a differential fragrance character. The initial fragrance impression is not distorted by the system of the present invention regardless of which point in use or delivery the system components are deployed, inter alia, pre-mixed, combined in a chamber, at said situs of contact or use.

The first aspect of the present invention relates to a fragrance delivery system comprising:

a) a pro-fragrance component comprising:
  i) P number of a pro-fragrance, a pro-accord, or mixtures thereof, which together release i number of fragrance raw materials, $f_i$, the index i identifies a particular fragrance raw material and the corresponding parameters, and at least a number j of said fragrance raw materials, $f_j$, satisfies the boundary condition defined by:

$$\chi_i > n(v_{Di})$$

wherein $\chi_i$ is 100% of the amount of the ith fragrance raw material, $f_i$, which is releasable from all of said pro-fragrances or pro-accords which are capable of releasing said ith fragrance raw material; $v_{Di}$ is the odor detection concentration of an ith fragrance raw material, whereby j number of said fragrance raw materials, $f_j$, satisfy said boundary condition; P is at least 1; i is at least 1; j is at least 1; n is a multiple of the odor detection concentration and is equal to at least 1;
  ii) optionally fragrance raw material release modifiers; and b) a free fragrance component comprising:
  i) an initial amount, $\epsilon_i$, of said j number of ith fragrance raw materials, $f_j$, which satisfy the boundary condition defined in (a); wherein $\epsilon_i$ of said ith fragrance raw material is defined as:

$$\epsilon_i \leq a(\chi_i)$$

a is 10;
  ii) optionally the balance one or more other fragrance raw materials, carriers, and adjunct ingredients.

The present invention further relates to compositions comprising the herein described fragrance delivery systems.

Another aspect of the present invention relates to a process for forming the fragrance delivery systems of the present invention.

These and other objects, features and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to compositions which are capable of delivering a sustained fragrance wherein the initial fragrance or accord impression is balanced, in one embodiment said fragrance is balanced during the entire use period of said fragrance. The present invention also provides a method for selecting fragrance raw materials and pro-fragrances and/or pro-accords in the correct relative amounts to provide the initial fragrance impression or character balance.

The present invention relates to the balance, and, therefore, the relationship between the amount of pro-fragrance present and the amount of free fragrance raw material present. A fragrance accord formulated with only pro-accords or pro-fragrances will have an initial bouquet or fragrance which is substantially different than the character which is present after the pro-fragrances or pro-accords begin to release their constituent fragrance raw materials. The present invention relates to a process for formulating a fragrance or perfume which is sustainable in its initial impression. The formulator can now surprisingly formulate a fragrance raw material comprising accord, or single fragrance, wherein the aroma is constant over a protracted period of time, and does not decay or become unbalanced in the manner which non-releasable perfume ingredients are used.

The systems of the present invention deliver a perfume scent, smell, bouquet, aroma, and the like, which has an enduring and balanced presence. Unlike direct fragrance raw material comprising perfume systems which diminish over a short period of time, the systems of the present invention sustain their original fragrance or character over a protracted period of time.

The systems of the present invention comprise two components prior to application or use of the compositions described herein. One component is the pro-perfume component which comprises pro-fragrances, pro-accords, and mixtures thereof which are capable after application, of releasing one or more fragrances raw materials.

The other component comprises a single fragrance raw material, or an admixture (accord) comprising two or more fragrance raw materials. It is one aspect of the present invention in that as the perfume ingredients of the initial perfume evaporate or are lost due to other means, an amount of these lost materials are released by the pro-perfume compounds to sustain the same level of the lost ingredients.

The formulator who wishes to employ pro-fragrances and pro-accords to provide enhanced duration of a balanced fragrance is faced with the fact that there are a multitude of pro-fragrance and pro-accord species, inter alia, esters, orthoesters, acetals, ketals, and that each of these chemical species has a different release rate depending upon the structure of the pro-perfume and the milieu in which the species is used, inter alia, as a fine fragrance, or in a cleaning composition.

The definitions herein below will aid the formulator in understanding the various aspects of the present invention and the means for determining the scope and utility of the present invention. For example, those of ordinary skill in the art recognize that the minimal amount of a fragrance raw material which can be perceived by the human is directly related to the odor detection threshold (ODT). However, fragrances raw materials act synergistically with one another, therefore, in some embodiments of the present invention, the amount of a fragrance raw material which is present in a composition or delivery system may be less than the ODT, solely because its presence affects the character of the other ingredients.

Definitions

Free Fragrance Component: The free fragrance component is the part of the fragrance delivery system which comprises free fragrance raw materials and their carriers or adjunct ingredients and is present in the system any time prior to use or execution of the delivery system. Depending upon the embodiment of the present invention, the free fragrance component can be admixed with the releasable fragrance component, kept separate, for example, in a separate reservoir or phase, or alternatively combined with the releasable fragrance component at the situs of use.

Releasable Fragrance Component: The releasable fragrance comprises pro-accords and pro-fragrances which release fragrance raw materials upon instigation of the release process, typically use by the consumer, and their optional carriers or adjunct ingredients. Depending upon the embodiment of the present invention, the releasable fragrance component can be admixed with the free fragrance component or kept separate, for example, in a separate reservoir or phase, or alternatively combined with the free fragrance component at the situs of use.

Free Fragrance Raw Material Concentration, $\epsilon$: This is the concentration of a fragrance raw material which is present as a free fragrance in a fragrance delivery system prior to intentional instigation of the release process, said process resulting in the release of additional fragrance raw materials. This concentration is critical to achieving the initial impression balance. It is critical for the proper formulation of the present delivery systems that $\epsilon$ is the amount of fragrance raw material present before the product is used for the first time.

Releasable Fragrance Raw Material Concentration, $\chi$: This is the concentration of a particular fragrance raw material which would be obtained upon 100% release of said fragrance raw material from all pro-fragrances or pro-accords that are present in the fragrance delivery system prior to intentional instigation of the release process. For example, this can be considered to be the "reservoired" amount of a fragrance raw material. Considered in another way, this is the "releasable" amount of a fragrance raw material. The system may comprise several pro-fragrances or pro-accords capable of releasing a fragrance raw material, $f_i$, however, due to the kinetics of release, each molecule may release said fragrance raw material at different rates. The value of $\chi$ is independent of the rate of release of the type of pro-perfume used by the formulator. The value $\chi$ does not include $\epsilon$, the concentration of said fragrance raw material which is present as free fragrance raw material.

Total Fragrance Raw Material Concentration, $\tau$: This is the total available concentration of a particular fragrance raw material and represents the sum of the free fragrance raw material and the deliverable fragrance raw material according to the equation:

$$\tau_i = \epsilon_i + \chi_i$$

where the subscript i refers to the ith fragrance raw material.

Odor Detection Concentration, $v_D$: The odor detection concentration (ODC) is defined herein as the lowest weight percent concentration of a fragrance raw material dissolved in dipropylene glycol (DPG) at which the average artisan of ordinary skill in perfume formulation can detect a fragrance raw material olfactory intensity of 10 on a scale of intensity ranging from 0 to 100.

Odor Saturation Concentration, $v_S$: The odor saturation concentration (OSC) is defined herein as the amount of fragrance raw material, expressed as weight percent dissolved in DPG, beyond which no further odor impression is provided as measured by the average artisan of ordinary skill in perfume formulation.

The chemical entities which deliver fragrance raw materials are pro-fragrances (releasing one fragrance raw material) and pro-accords (releasing multiple fragrance raw materials). The term "pro-perfume" is use interchangeably with the terms pro-fragrance and pro-accord and is used to connote the concept of ingredients which are deliverable from a precursor molecule which must break down to release the constituent fragrance raw material. Pro-perfumes (pro-fragrances and pro-accords) are disclosed in U.S. Pat. No. 5,559,088 Severns et al., issued Sep. 24, 1996; U.S. Pat. No. 5,562,847 Waite et al., issued Oct. 8, 1996; U.S. Pat. No. 5,652,205 Hartman et al., issued Jul. 29, 1997; U.S. Pat. No. 5,710,122 Sivik et al., issued Jan. 20, 1998; U.S. Pat. No. 5,716,918 Sivik et al., issued Feb. 10, 1998; U.S. Pat. No. 5,721,202 Waite et al., issued Feb. 24, 1998; U.S. Pat. No. 5,744,435 Hartman et al., issued Apr. 25, 1998; U.S. Pat. No. 5,756,827 Sivik, issued May 26, 1998; U.S. Pat. No. 5,710, 122 Sivik et al., issued Jan. 20, 1999; U.S. Pat. No. 5,919, 752 Morelli et al., issued Jul. 6, 1999; U.S. Pat. No. 5,965,767 Sivik et al., issued Oct. 12, 1999; U.S. Pat. No. 6,013,618 Morelli et al., issued Jan. 11, 2000; U.S. Pat. No. 6,077,821 Morelli et al., issued Jun. 20, 2000; U.S. Pat. No. 6,083,892 Severns et al., issued Jul. 4, 2000; U.S. Pat. No. 6,087,322 Morelli et al., issued Jul. 11, 2000; U.S. Pat. No. 6,093,691 Sivik et al., issued Jul. 25, 2000; U.S. Pat. No. 6,100,233 Sivik et al., issued Aug. 8, 2000; U.S. Pat. No. 6,114,302 Morelli et al., issued Sep. 5, 2000; U.S. Pat. No. 6,126,953 Costa et al., issued Oct. 3, 2000; U.S. Pat. No. 6,147,037 Gardlik et al., issued Nov. 14, 2000; U.S. Pat. No. 6,150,310 Sivik et al., issued Nov. 21, 2000; U.S. Pat. No. 6,156,710 Sivik et al., issued Dec. 5, 2000, U.S. Pat. No. 6,165,953 Gardlik et al., issued Dec. 26, 2000; U.S. Pat. No. 6,177,389 Morelli et al., issued Jan. 23, 2001; U.S. Pat. No. 6,184,188 Severns et al., issued Feb. 6, 2001; Provisional U.S. Patent Application No. 60/246,811 filed Nov. 8, 2000; all of which are included herein by reference.

The present invention relates to a process for providing enhanced duration fragrance delivery systems wherein said delivery systems have a non-distorted initial fragrance impression.

Step (a): This step of the present invention relates to selecting P number of pro-fragrances and/or pro-accords which will comprise the pro-perfume aspect of the delivery system. The systems comprise from 1 to an infinite number of pro-fragrances depending upon the selection of the formulator. However, the formulator will typically encounter fragrances and accords having varying complexities. For example, simple delivery systems useful in soaps and cosmetics may comprise from 2 to 6, in another embodiment to 10 fragrance raw materials whereas fine fragrances may comprise as many as 50 fragrance raw materials.

Any pro-fragrance or pro-accord, as described in the cited references herein above, are useful for step (a). In fact, the formulator may customize a pro-fragrance in any manner necessary to obtain the desired release rate or profile. A non-limiting example of this customization may include synthesizing an orthoester pro-fragrance from two or more fragrance raw material alcohols as described in one or more of the references cited herein above.

Provisional U.S. Patent Application No. 60/246,811 filed Nov. 8, 2000 as cited herein above, relates to photo labile pro-fragrances and pro-accords which can be suitably used to formulate the materials selected for inclusion into step (a).

Each pro-fragrance or pro-accord selected releases at least one fragrance raw material, f, wherein said fragrance raw material is capable of satisfying the boundary condition defined by the formula:

$$\chi > n(v_D)$$

wherein $\chi$ is the weight percent concentration of the fragrance raw material which is obtained upon 100% release of said fragrance raw material from said pro-fragrances. The amount of fragrance raw material represented by $\chi$ is that amount of fragrance raw material which is held "in reserve." Alternatively this amount $\chi$ can be considered to be the "potential amount" or "releasable amount" of the fragrance raw material which is present in the form of a pro-fragrance or pro-accord. The term $v_D$ is the odor detection concentration (ODC) as defined herein for said fragrance raw material, f. Each fragrance raw material will have its own unique ODC.

The value of $\chi$ of a fragrance raw material, f, will always be greater than the ODC of the particular fragrance raw material (FRM) because if the concentration of the particular FRM, f, falls below the value of $v_D$, the FRM will not be present at a level high enough concentration to be perceived by the human olfactory senses.

The present invention in its broadest sense relates to the release of i number of fragrance raw materials, $f_i$, wherein i is at least 1. For an accord i has the value of at least 2. For example, a system comprising ten (i=10) FRM's will have releasable fragrance raw materials $f_1+f_2+ \ldots f_{10}$, thereby providing a fragrance accord comprising ten different perfume raw material ingredients. These FRM's may be released from any number or combination of pro-accords or pro-fragrances. For example, trisgeraniol orthoformate and digeranyl hexanoate acetal each release the fragrance raw material geraniol and both may be present together in a fragrance enhancing system, whereby the formulator, by taking into account the differential release rates of geraniol by these two species, and their relative stability once applied to a situs, may include both of these pro-perfumes into a release system as a suitable source of geraniol.

Therefore, in the systems of the present invention, one or more pro-fragrances, P in number, are capable of releasing one or more fragrance raw materials, $f_i$, wherein at least a number j, wherein j is at least one, of said fragrance raw materials $f_i$ are capable of satisfying the boundary conditions defined by the formula:

$$\chi_i > n(v_{Di})$$

wherein $\chi_i$ is the weight percent concentration of the ith fragrance raw material which is obtained upon 100% release of said fragrance raw material released from P number of pro-fragrances wherein $v_{Di}$ is the odor detection concentration of said ith fragrance raw material.

The index n is a factor which relates to the amount of fragrance raw material which is releasable and indicates the relative amount of a fragrance raw material which is to be released. One aspect of the present invention relates to perfume systems which have the level of a FRM in a releasable form (in the form of a pro-perfume) that is twice the ODC (n=2). Other embodiments employ n=5 or greater. Without wishing to be limited by theory, by having a greater amount of a FRM in reserve (n>1), the formulator can sustain longer the level of the fragrance.

In one embodiment of the present invention the number of fragrance raw materials which are released are at least 2 (i=2), in yet another at least 5 are released (i=5).

It will be noted by the formulator, that the value for n of each FRM does not have to be the same. A fragrance raw material having high volatility will need to have more releasable (potential FRM) perfume ingredient in the form of a pro-perfume material because of the short residence time (high volatility) of the molecule.

The following is a non-limiting example which points out the relationship between the FRM, f, and the ODC. A formulator selects a pro-fragrance having the formula:

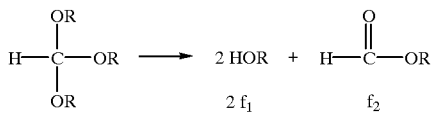

in order to release two fragrance raw materials, $f_1$ and $f_2$, according to the scheme above wherein two moles of alcohol are released and one mole of formate ester. For the sake of example only, if the fragrance raw material alcohol, HOR, which is released has a $v_{Di}$ equal to 0.002 mol/l, and the formulator wishes only the ODC amount of the fragrance raw material to be present, then the concentration of the pro-fragrance would then be 0.001 mol/l since the pro-fragrance is sufficient to provide the ODC concentration of said alcohol. However, if the formulator desires twice the ODC level of this alcohol to be present (n=2) then the concentration of the pro-fragrance would be twice the amount or 0.002 mol/l. This example provides the amounts as expressed in moles, however, the formulator may choose weight %, or any other means to express the amount of compounds necessary. In one embodiment, n=1, while in another embodiment of the present invention n=2. Yet another embodiment wherein the amount of released fragrance raw material, $f_i$, is desired to be high, n=5 or above.

Step (b): This step relates to combining the pro-perfume ingredients of the systems of the present invention with the "free fragrance raw materials" which comprise the initial fragrance and in determining the relative amount of each fragrance raw material which must be present in the initial free fragrance component. In this step P number of pro-fragrances which release at least one of said ith fragrance raw materials, fi, is used to determine the initial free concentration, $\epsilon_i$, of said ith fragrance raw materials, fi. For the purposes of the present invention the term, $\epsilon_i$, is defined herein as:

$$\epsilon_i \leq a(\chi_i)$$

wherein a is the factor which relates to the amount of free fragrance raw material present in the initial fragrance delivery system, prior to initiation of FRM release by the pro-perfumes, is less than or equal to five times the amount of a particular FRM, $f_i$, which is releasable by all of the pro-perfume ingredients which comprise the fragrance enhancement system. The index a is equal to 10. However, in other embodiments of the present invention, a may have a value less than 10.

It is important to note that some amount of the free fragrance, $\epsilon$, initially present in the systems of the present invention, may derive from the source of the pro-perfume ingredients. For example, a pro-perfume which releases geraniol may comprise free geraniol due to the method of preparation, initial breakdown, etc. The formulator will include this fraction of geraniol into account when determining the amount of the free geraniol, $\epsilon$, in the initial formulation. For the purposes of the present invention, the initial amount of free fragrance, $\epsilon$, for a fragrance raw material will never be greater than 25% of the composition into which the fragrance raw material is formulated or into which the system of the present invention is formulated.

For one embodiment of the present invention, the manner in which the amount of releasable fragrance raw materials, $\chi_i$, is related to the initial free concentration, $\epsilon_i$, of said ith fragrance raw materials and is defined by the formula:

$$(0.1)^a(\chi_i) \leq \epsilon_i$$

wherein a is 5. In one embodiment of the present invention all fragrance raw materials have an index a less than or equal to 3. Another aspect of the present invention relates to a system which delivers fragrance raw materials wherein at least one of the fragrance raw materials, $f_i$, has an index a equal to or less than 1.

As described herein above, the amount $\epsilon$ which is present is the amount of a free fragrance raw material which is present at the moment the system is delivered under use conditions for the first time. For example, the formulator, knowing a period of time will elapse from the point of manufacture to use by the consumer or operator, may have the initial amount of a fragrance raw material formulated in a deliverable form. For example, as a pro-fragrance which will rapidly break down after formulation to deliver a fragrance raw material which will be present in an amount $\epsilon$ at the time the system will be delivered for the first time. Therefore, the term initial amount $\epsilon$ relates to the amount of a fragrance raw material which is present at the moment the system is delivered for use the first time.

Method for Determining Odor Detection and Odor Saturation Concentrations

To determine the ODC and the OSC for a given fragrance raw material f, an Olfactory Intensity vs. Log Concentration curve is constructed. This process is comprised of both an initial and a final determination.

Initial Determination: Initially, the rough shape of the curve is determined by dissolving pure f in pure DPG at concentrations of 0.0000001, 0.000001, 0.00001, 0.0001, 0.001, 0.01, 0.1, 1.0 and 10 weight percent. Olfactory Intensity is graded for each solution from 0 to 100 by a panel of at least three expert graders composed of average artisans of ordinary skill in perfume formulation. The Olfactory Intensity at any concentration is taken to be the mean of the individual grades at that concentration. Table I below gives Olfactory Intensity grades determined in this manner for two common fragrance raw materials at three different weight percent concentration in DPG.

TABLE I

Olfactory Intensity Grades for Two Common Fragrance Raw Materials

| Fragrance Raw Material, $f$ | $[f]$* | Olfactory Intensity |
| --- | --- | --- |
| 2,4-dimethyl-3-cyclohexene-1-carboxaldehyde | 0.0005 | 30 |
| 2,4-dimethyl-3-cyclohexene-1-carboxaldehyde | 0.001 | 50 |
| 2,4-dimethyl-3-cyclohexene-1-carboxaldehyde | 0.003 | 70 |
| 1-(2,6,6-trimethyl-3-cyclohexen-1-yl)-2-buten-1-one | 0.00004 | 30 |
| 1-(2,6,6-trimethyl-3-cyclohexen-1-yl)-2-buten-1-one | 0.00009 | 50 |
| 1-(2,6,6-trimethyl-3-cyclohexen-1-yl)-2-buten-1-one | 0.0005 | 70 |

*Wt. % concentration of the fragrance raw material in DPG.

An example of the data used to construct a rough curve for a third common fragrance raw material, 2,6-dimethyl-5-heptenal, is given in Table II below.

TABLE II

Initial Determination:
Olfactory Intensity Grades for 2,6-Dimethyl-5-heptenal

| Entry | $[f]$* | Log $[f]$ | Olfactory Intensity |
| --- | --- | --- | --- |
| 1 | 0.0000001 | −7.0 | 0 |
| 2 | 0.000001 | −6.0 | 0 |
| 3 | 0.00001 | −5.0 | 0 |
| 4 | 0.0001 | −4.0 | 10 |

TABLE II-continued

Initial Determination:
Olfactory Intensity Grades for 2,6-Dimethyl-5-heptenal

| Entry | [f]* | Log [f] | Olfactory Intensity |
|---|---|---|---|
| 5 | 0.001 | −3.0 | 55 |
| 6 | 0.01 | −2.0 | 81 |
| 7 | 0.1 | −1.0 | 83 |
| 8 | 1.0 | 0.0 | 84 |
| 9 | 10.0 | 1.0 | 84 |

*Wt. % concentration of the fragrance raw material in DPG.

The Initial Determination gives the general shape of the curve and is used to establish which of the nine concentrations (Entries 1–9 in Table II) will be used for the starting fragrance raw material concentration, $[f]_{start}$, and which will be used for the upper concentration limit, $[f]_{limit}$, in the Final Determination. The highest concentration of fragrance raw material that gives an Olfactory Intensity below 5 is chosen as the starting concentration for the Final Determination. In the example given, $[f]_{start}$ is 0.00001 wt. % of 2,6-dimethyl-5-heptenal in DPG (Table II, Entry 3). The lowest concentration of fragrance raw material above $[f]_{start}$ for which the Olfactory Intensity of the two immediately adjacent concentrations are separated by less than 5 is chosen as the upper concentration limit for the Final Determination. In the example given, $[f]_{limit}$ is 0.10 wt. % of 2,6-dimethyl-5-heptenal in DPG (Table II, Entry 7).

Final Determination: In constructing the final curve, multiples of said starting concentration are used. The concentrations used are the starting concentration, $[f]_{start}$=1c, and the multiples 5c, 10c, 20c, 40c, 80c, 160c, 320c, 640c, 1280c, 2560c, 5120c, 1024c, 2048c, 4096c, etc., up to and including the point where the multiple first surpasses $[f]_{limit}$. Olfactory Intensity is graded for each solution from 0 to 100 by a panel of at least three expert graders composed of average artisans of ordinary skill in perfume formulation. The Olfactory Intensity at any concentration is taken to be the mean of the individual grades at that concentration. An example of the data used to construct a final curve for 2,6-dimethyl-5-heptenal is shown in Table III below

TABLE III

Final Determination:
Olfactory Intensity Grades for 2,6-Dimethyl-5-heptenal

| Entry | [f]* | Log [f] | Olfactory Intensity |
|---|---|---|---|
| 1 | 0.00001 | −5.00 | 0 |
| 2 | 0.00005 | −4.30 | 6 |
| 3 | 0.0001 | −4.00 | 10 |
| 4 | 0.0002 | −3.70 | 19 |
| 5 | 0.0004 | −3.40 | 33 |
| 6 | 0.0008 | −3.10 | 50 |
| 7 | 0.0016 | −2.80 | 64 |
| 8 | 0.0032 | −2.50 | 74 |
| 9 | 0.0064 | −2.19 | 78 |
| 10 | 0.0128 | −1.89 | 81 |
| 11 | 0.0256 | −1.59 | 83 |
| 12 | 0.0512 | −1.29 | 83 |
| 13 | 0.1024 | −0.99 | 84 |

*Wt. % concentration of the fragrance raw material in DPG.

The Final Determination yields values for the ODC and the OSC. The odor detection concentration (ODC) is defined herein as the lowest weight percent concentration, above $[f]_{start}$, of a fragrance raw material dissolved in dipropylene glycol (DPG) at which the fragrance raw material olfactory intensity is 10 on a scale of intensity ranging from 0 to 100. The determination may require linear interpolation between two consecutive concentrations where one has an olfactory intensity below 10 and the other above 10. For 2,6-dimethyl-5-heptenal, the ODC as determined above is 0.0001 wt. % (Table III, Entry 3). The odor saturation concentration (OSC) is defined as the lowest concentration of a fragrance raw material above the ODC for which the Olfactory Intensity of the two immediately adjacent concentrations are separated by less than 5. For 2,6-dimethyl-5-heptenal, the OSC as determined above is 0.0256 wt. % (Table III, Entry 11).

Mixtures of fragrance materials are known by those skilled in the art of fragrances and perfumes as "accords". The term "accord" as used herein is defined as "a mixture of two or more 'fragrance raw materials' which are artfully combined to impart a pleasurable scent, odor, essence, or fragrance characteristic." For the purposes of the present invention "fragrance raw materials" are herein defined as compounds having a molecular weight of at least 100 g/mol and which are useful in imparting an odor, fragrance, essence, or scent either alone or in combination with other "fragrance raw materials."

Typically "fragrance raw materials" comprise inter alia alcohols, ketones, aldehydes, esters, ethers, nitrites, and cyclic and acyclic alkenes such as terpenes. A listing of common "fragrance raw materials" can be found in various reference sources, for example, "Perfume and Flavor Chemicals", Vols. I and II; Steffen Arctander Allured Pub. Co. (1994) and "Perfumes: Art, Science and Technology"; Müller, P. M. and Lamparsky, D., Blackie Academic and Professional (1994) both incorporated herein by reference.

Prior to the advent of pro-fragrances and pro-accords, the formulator of perfumes and fragrances delivered a scent which immediately began to diminish due to evaporation. However, with the use of fragrance raw material releasing components, the particular component (fragrance raw material) can be continually replenished by break down of the pro-fragrance or pro-accord. However, when the pro-fragrance or pro-accord comprising composition is applied, the concentration of the ith free fragrance raw material, $\epsilon_i$, when taken together with the concentration of the ith fragrance raw material released subsequent to intentional instigation of the release process, provides an initial in-use concentration of the ith fragrance raw material which can distort the initial fragrance impression. In many instances, fragrance raw materials in a concentration which even approaches the OSC have a negative fragrance impact. For example, skatole, 3-methyl-1H-indole, which is a component responsible for the foul odor of feces, when used at concentrations near the ODC, is a fragrance raw material which can be used in perfumery to provide certain desirable notes. However, the presence of this component at higher levels, even those remotely approaching the OSC, either by formulation or by premature-release via a pro-fragrance, would be detrimental to the fragrance character.

The systems of the present invention which are capable of providing a non-distorted initial fragrance impression comprise:

a) a pro-fragrance component comprising:
i) a number, P, of pro-fragrances, wherein P is 1 or greater, each pro-fragrance capable of releasing at least one fragrance raw material, $f_i$, wherein at least one of said fragrance raw materials $f_i$ are capable of being so released that the fragrance raw material released has a fragrance profile satisfying the boundary condition defined by the following:

$$\chi_i > n(v_{Di})$$

wherein i is an index number relating to a particular fragrance raw material, $\chi_i$ is the weight percent concentration of the ith fragrance raw material which is releasable from all of one or more of said P pro-fragrances; n is a multiple of the odor detection concentration and is equal to 1; $v_{Di}$ is the odor detection concentration of said ith fragrance raw material; and ii) optionally fragrance raw material release modifiers;

b) a free fragrance component comprising:
i) fragrance raw materials constituting a free fragrance accord, wherein each fragrance raw material has a concentration $\epsilon$ expressed as a weight % of said fragrance delivery system, and provided when at least m number of said ith fragrance raw materials is present at a concentration $\epsilon_i$ within the boundary conditions described by the formula:

$$\log v_{Si} - \tfrac{1}{2}\log v_{Di} > \log \epsilon_i > \log v_{Si} + \tfrac{1}{2}\log v_{Di}$$

wherein $v_{Si}$ is the odor saturation concentration of said ith fragrance raw material; $v_{Di}$ is the odor detection concentration of said ith fragrance raw material; m is 1; and ii) optionally carriers and adjunct ingredients.

In one embodiment of the present invention the number of fragrance raw materials which are present, m, is at least 2.

The systems of the present invention also relate to an aspect wherein one pro-fragrance is present. For example a system comprising:

a) a pro-fragrance component comprising:
i) a pro-fragrance which releases a fragrance raw material, f, wherein said f is selected from the group consisting of alcohols, ketones, aldehydes, esters, nitrites, terpenes, wherein said fragrance raw material satisfies the boundary condition defined by the following:

$$\chi > n(v_D)$$

wherein $\chi$ is the weight percent concentration of said fragrance raw material which is releasable by said pro-fragrance; n is a multiple of the odor detection concentration of said fragrance raw material and is at least 1; $v_D$ is the odor detection concentration of said fragrance raw material;

ii) optionally fragrance raw material release modifiers;

b) a free fragrance component comprising:
i) an amount, $\epsilon$, of said fragrance raw material, f, wherein $\epsilon$ the weight % of free fragrance raw defined as $$\epsilon \leq a(\chi)$$

wherein a is at least 5, and the amount $\epsilon$ is defined by the boundary conditions described by the formula:

$$\log v_{Si} - \tfrac{1}{2}\log v_{Di} > \log v_{Si} + \tfrac{1}{2} \log v_{Di}$$

wherein $v_{Si}$ is the odor saturation concentration of said ith fragrance raw material; $v_{Di}$ is the odor detection concentration of said ith fragrance raw material; and ii) optionally carriers and adjunct ingredients.

Another aspect of the present invention relates to a system comprising:

a) a pro-fragrance component comprising:
i) at least one pro-fragrance or pro-accord which is a photo-labile material which releases a fragrance raw material, f, wherein said f is selected from the group consisting of alcohols, ketones, aldehydes, esters, nitrites, terpenes, wherein said fragrance raw material satisfies the boundary condition defined by the following:

$$\chi > n(v_D)$$

wherein $\chi$ is the weight percent concentration of said fragrance raw material which is releasable by said pro-fragrance; n is a multiple of the odor detection concentration of said fragrance raw material and is at least 1; $v_D$ is the odor detection concentration of said fragrance raw material;

ii) optionally fragrance raw material release modifiers;

b) a free fragrance component comprising:
i) an amount, $\epsilon$, of said fragrance raw material, f, wherein $\epsilon$ the weight % of free fragrance raw defined as $$\epsilon \leq a(\chi)$$

wherein a is at least 5, and the amount $\epsilon$ is defined by the boundary conditions described by the formula:

$$\log v_{Si} - \tfrac{1}{2}\log v_{Di} > \log \epsilon_i > \log v_{Si} + \tfrac{1}{2}\log v_D$$

wherein $v_{Si}$ is the odor saturation concentration of said ith fragrance raw material; $v_{Di}$ is the odor detection concentration of said ith fragrance raw material; and ii) optionally carriers and adjunct ingredients.

Another aspect of the present invention relates to a system comprising:

a) a pro-fragrance component comprising:
i) a pro-accord which releases i number of fragrance raw materials, $f_i$, wherein said f is selected from the group consisting of alcohols, ketones, aldehydes, esters, nitrites, terpenes, wherein at least one of said fragrance raw materials satisfies the boundary condition defined by the following:

$$\chi_i > n(v_{Di})$$

wherein $\chi_i$ is the weight percent concentration of one of said fragrance raw materials capable of being released by said pro-accord; n is a multiple of the odor detection concentration of said fragrance raw material and is at least 1; $v_{Di}$ is the odor detection concentration of at least one of said fragrance raw materials;

ii) optionally fragrance raw material release modifiers;

b) a free fragrance component comprising:
i) an amount, $\epsilon_i$, of said fragrance raw material, $f_i$, wherein $\epsilon_1$, is the weight % of at least one free fragrance raw defined as $$\epsilon_i \leq a(\chi_i)$$

wherein a is at least 5, and the amount $\epsilon_i$ for each $f_i$ satisfying the conditions of (a)(i) is defined by the boundary conditions described by the formula:

$$\log v_{Si} - \tfrac{1}{2}\log v_{Di} > \log \epsilon_i > \log v_{Si} + \tfrac{1}{2}\log v_{Di}$$

wherein $v_{Si}$ is the odor saturation concentration of said ith fragrance raw material; $v_{Di}$ is the odor detection concentration of said ith fragrance raw material which satisfies the conditions of (a)(i); and ii) optionally carriers and adjunct ingredients.

The following is a non-limiting example of the process for selecting the components of the present invention. A fragrance raw material having an odor detection concentration of $10^{-4}$ (0.0001 weight percent in DPG) and an odor saturation concentration of $10^{-2}$ (0.01 weight percent in DPG) is substituted into the equation:

$$\log v_S - \tfrac{1}{2}\log v_D > \log \epsilon > \log v_S + \tfrac{1}{2}\log v_D$$

to give:

$$\log 10^{-2} - \tfrac{1}{2}\log 10^{-4} > \log \epsilon > \log 10^{-2} + \tfrac{1}{2}\log 10^{-4} (-2) - \tfrac{1}{2}(-4) > \log \epsilon > (-2) + \tfrac{1}{2}(-4)\ 0 > \log \epsilon > -4$$

therefore, the preferred range at which said fragrance raw material must be present in the fragrance delivery system of the present invention is from $1 \times 10^{-4}\%$ by weight to 1% by weight.

FORMULATIONS

The process of the present invention and the fragrance delivery systems derived therefrom, can be used to enhance the duration of any composition which comprises a fragrance or perfume component.

One aspect relates to a fine fragrance component which comprise:

A) from about 0.001%, in another embodiment from about 0.01% to about 25%, whereas another aspect comprises from about 0.1% to about 10%, yet another aspect relates to embodiments having from about 1% to about 5%, by weight, of a pro-perfume component comprising:

i) at least one pro-fragrance or pro-accord which releases a fragrance raw material, f, wherein said f is selected from the group consisting of alcohols, ketones, aldehydes, esters, nitrites, terpenes, wherein said fragrance raw material satisfies the boundary condition defined by the following:

$$102 > n(v_D)$$

wherein $\chi$ is the weight percent concentration of said fragrance raw material which is releasable by said pro-fragrance; n is a multiple of the odor detection concentration of said fragrance raw material and is at least 1; $v_D$ is the odor detection concentration of said fragrance raw material;

ii) optionally fragrance raw material release modifiers;

B) a free fragrance raw material component wherein each fragrance raw material f is present in an initial concentration, $\epsilon$, such that the wt % of f present in the initial composition satisfies the boundary conditions:

$$\epsilon \leq a(\chi)$$

wherein a is at least 5; and

C) the balance carriers and adjunct ingredients.

A specific embodiment of the above formulation relates to compositions comprising from about 0.01% to about 0.2% by weight, of a pro-fragrance component.

Another aspect of the present invention relates to enhanced duration fine fragrances which comprise an admixture of fragrance raw materials which form the initial perfume accord which is sustained by the fragrance raw material releasing systems of the present invention.

The formulator can provide an enhanced fragrance accord with a system comprising:

A) from about 0.001%, in another embodiment from about 0.1% to about 90%, whereas another aspect comprises from about 10% to about 75%, by weight, of a pro-perfume component comprising:

i) an admixture of, P, number of pro-fragrances, pro-accords, and mixtures thereof, which constitutes a pro-perfume ingredient, wherein said pro-perfume ingredient releases fragrance raw materials, $f_i$, wherein i is an index which designates a particular fragrance raw material, said $f_i$ is selected from the group consisting of alcohols, ketones, aldehydes, esters, nitrites, terpenes; and wherein the wt % of the ith said fragrance raw material which is releasable from said P number of pro-fragrances, pro-accords, and mixtures thereof, each satisfies the boundary condition defined by the following:

$$\chi_i > n(v_{Di})$$

wherein $\chi$ is the wt % concentration of said fragrance raw material $f_i$ which is releasable by said pro-fragrance; n is a multiple of the odor detection concentration of said fragrance raw material and is at least 1; $v_D$ is the odor detection concentration of said fragrance raw material; P is at least 2;

ii) optionally fragrance raw material release modifiers;

B) a free fragrance raw material component wherein each fragrance raw material $f_i$ is present in an initial concentration, $\epsilon_i$, such that the wt % of $f_i$ present in the initial composition satisfies the boundary conditions:

$$\epsilon_i \leq a(\chi_i)$$

wherein a is at least 5; and provided $\epsilon_i$, does not comprise greater than 25% by weight, of a composition comprising said system; and C) the balance carriers and adjunct ingredients.

A non-limiting example of a composition which comprises the system of the present invention is one wherein a fragrance raw material is present to signal to the user that an active ingredient is present. By using the process of the present invention the formulator can employ an enhanced fragrance delivery system which matches the lifetime of the active ingredient.

For example, a composition comprising:

A) from about 0.01% to about 75% by weight, of one or more active ingredients;

B) from about 0.01% by weight, of a fragrance delivery system comprising:

a) a pro-fragrance, P, which releases fragrance raw material, f, wherein P is present in an amount such that the releasable fragrance raw material concentration, $\chi$, is defined by the relationship:

$$\chi > n(v_D)$$

wherein $v_D$ is the odor detection concentration of the fragrance raw material, f, n is at least 1;

b) said fragrance raw material, f, in an initial concentration amount, $\epsilon$, wherein $\epsilon$ is defined as:

$$\epsilon \leq q$$

wherein q is the weight percent of said active ingredient containing composition and equals 25; and C) the balance carriers and adjunct ingredients.

For the purposes of the present invention the term "active ingredient" means any material which provides a benefit and which would be delivered to a situs with a fragrance delivery system. Active ingredients include, anti microbials, anti bacterials, soaps, astringents, emollients, skin protectants, and the like.

In other embodiments of this aspect of the present invention, the value of q is less than or equal to 15% of the final composition. For compositions employing an accord, one embodiment of the present invention comprises a fragrance delivery system wherein the value of q for each fragrance raw material present in the initial accord is less than or equal to 10% by weight, of the composition.

The following is a non-limiting example of a system according to the present invention.

TABLE IV

| Ingredients | Weight % | | | | | | |
| --- | --- | --- | --- | --- | --- | --- | --- |
| | 1 | 2 | 3 | 4 | 5 | 6 | 7 |
| Pro-fragrance component | | | | | | | |
| Pro-fragrance[1] | 0.4 | 1.0 | 0.19 | — | 0.35 | — | — |
| Pro-fragrance[2] | 0.2 | 2.0 | 0.19 | — | — | — | — |
| Pro-fragrance[3] | 0.2 | 2.0 | — | 0.2 | — | — | — |
| Pro-fragrance[4] | — | 2.0 | 0.19 | 0.4 | — | — | — |
| Pro-fragrance[5] | — | — | 0.37 | — | — | 0.25 | — |
| Pro-fragrance[6] | | | | | | | 0.5 |
| Free fragrance component | | | | | | | |
| Damascone | 0.0001 | 0.001 | 0.0005 | — | 0.0005 | — | — |
| Melonal | 0.05 | 0.1 | 0.002 | — | — | — | — |
| Triplal | 0.01 | 0.1 | 0.008 | 0.007 | — | — | — |
| Undecavertol | — | 0.5 | — | 0.1 | — | — | — |
| Geraniol | — | — | 0.03 | — | — | 0.02 | — |
| 9-Decen-1-ol | — | — | — | — | — | — | 0.0025 |
| Coumarin | — | — | — | — | — | — | 0.0001 |
| Additional free fragrance raw materials[7] | 13.8 | 15.2 | 17.0 | 15.1 | 14.5 | 16.0 | 12.3 |
| Carrier[8] | balance | balance | balance | balance | balance | balance | balance |

[1]Pro-fragrance which releases α-damascone, for example

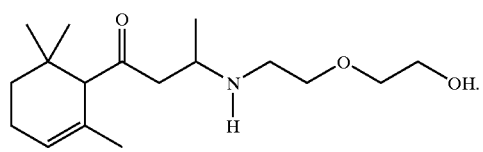

[2]Pro-fragrance which releases melonal, for example

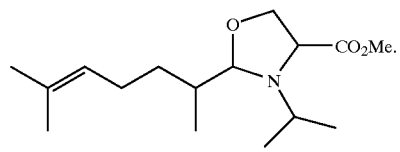

[3]Pro-fragrance which releases triplal, for example

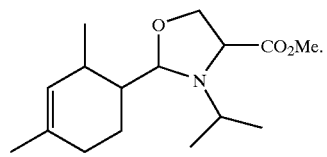

TABLE IV-continued

| | Weight % | | | | | | |
|---|---|---|---|---|---|---|---|
| Ingredients | 1 | 2 | 3 | 4 | 5 | 6 | 7 |

[4] Pro-fragrance which releases undecavertol, for example

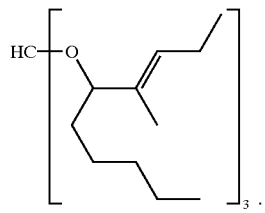

[5] Pro-fragrance which releases geraniol; for example

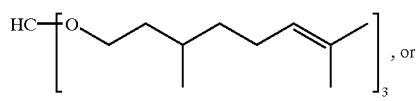

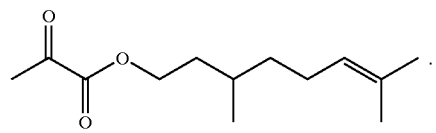

[6] Pro-fragrance which releases 9-decen-1-ol; for example

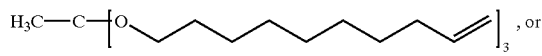

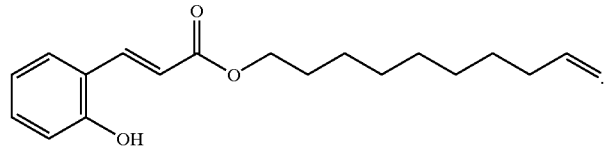

[7] Conventional fragrance accord.
[8] Ethanol:water mixture (between 100:0 and 50:50).

The enhanced duration fragrance delivery systems of the present invention are suitable for use in laundry products, dish soap compositions, or hard surface cleaners. Non-limiting examples include liquid and granular laundry detergent compositions, fabric softeners both rinse-added and dryer-added compositions, as well as pre-treatments and post-treatment refreshers. Non-limiting examples of hard surface cleaners includes scouring powders, spray-on liquids, and the like.

The following table provides non-limiting examples of Heavy Duty Liquid laundry detergent compositions comprising a fragrance delivery system according to the present invention.

TABLE V

| | weight % | | |
|---|---|---|---|
| Ingredients | 2 | 3 | 4 |
| Sodium $C_{12}$–$C_{15}$ alcohol ethoxy (1.25) sulfate[1] | 18 | 18 | 18 |
| Linear alkylbenzene sulphonate | 5.8 | 5.8 | 5.8 |
| $C_8$–$C_{10}$ amide nonionic surfactant[2] | 1.17 | 1.4 | 1.4 |
| $C_{12}$–$C_{14}$ alkyl ethoxy (7.0) alcohol[3] | 4.1 | 2.8 | 2.8 |
| Builder | 12.6 | 11 | 11 |
| Protease[4] | 0.74 | 0.74 | 0.74 |
| Amylase[5] | 0.072 | 0.072 | 0.072 |
| Amylase[6] | 0.144 | — | — |
| Amylase[7] | — | 0.105 | 0.105 |
| Cellulase[8] | 0.028 | 0.028 | 0.028 |
| Cellulase[9] | 0.12 | — | — |
| Lipolase[10] | 0.06 | — | — |
| Mannanase[11] | — | 0.28 | 0.28 |

TABLE V-continued

| Ingredients | weight % | | |
|---|---|---|---|
| | 2 | 3 | 4 |
| Boric acid[12] | 2 | 2 | 2 |
| Ca formate/CaCl$_2$ | 0.02 | 0.02 | 0.02 |
| Dispersant[13] | 0.65 | 0.90 | — |
| Dispersant[14] | 0.68 | 0.70 | 0.7 |
| Soil Release Polymer[15] | 0.147 | — | — |
| Polyamine[16] | 1.5 | 2.0 | 1.4 |
| Chelant[17] | 0.61 | 0.30 | 0.3 |
| Chelant[18] | 0.35 | 0.35 | 0.35 |
| Optical brightener[19] | 0.144 | 0.144 | 0.144 |
| Pro-fragrance component | | | |
| Pro-fragrance[20] | 0.02 | 0.04 | — |
| Pro-fragrance[21] | — | 0.2 | — |
| Pro-fragrance[22] | — | 0.02 | — |
| Pro-fragrance[23] | — | 0.05 | 0.2 |
| Free fragrance Component | | | |
| Damascone | 0.005 | 0.01 | — |
| Melonal | — | 0.05 | — |
| Triplal | — | 0.02 | — |
| 9-Decen-1-ol | — | 0.01 | 0.05 |
| Coumarin | — | — | 0.01 |
| Additional free fragrance raw materials[24] | 0.25 | 0.2 | 0.3 |
| Minors[25] | balance | balance | balance |

[1]Can comprise either linear or mid-chain branched alkyl units
[2]3-N'-(C$_8$–C$_{10}$ branched alkanoyl)-N,N-dimethyl-1,3-diaminopropane.
[3]NEODOL 24-7 ex Shell Oil Co.
[4]Protease enzyme from *Bacillus Amyloliquefaciens* as described
in EP 0 130 756 B1 published Jan. 9, 1985.
[5]Termamyl ® available ex Novo.
[6]Duramyl ® available ex Novo.
[7]Natalase ® ex Novo as described in WO 95/26397 and WO. 96/23873.
[8]Carezyme ® available ex Novo.
[9]Endo A ® available ex Novo.
[10]Lipolase Ultra available ex Novo.
[11]Mannanase enzyme originating from *Bacillus sp.* I633 available ex Novo, 2.5% active
[12]As part of an enzyme stabilizing system.
[13]PEI 189 E15-E18 according to U.S. Pat. No. 4,597,898 Vander Meer,
issued Jul. 1, 1986.
[14]Ethoxylated Polyalkylene Dispersant: PEI 600 E20.
[15]Dimethylterephthalate, 1,2-propylene glycol, methyl capped PEG
co-polymer according to U.S. Pat. No. 4,702,857 Gosselink, issued
Oct. 27, 1987.
[16]Zwitterionic polymer: bis(hexamethylene)triamine, ethoxylated to average E20 per NH,
quaternized to 90%, and sulfated to approximately 35%–40%.
[17]Diethylene triamine penta(methyl phosphonic) acid (DTPMP).
[18]Hydroxyethanedimethylenephosphonic acid
[19]FWA-36.
[20]Pro-fragrance which releases α-damascone, for example

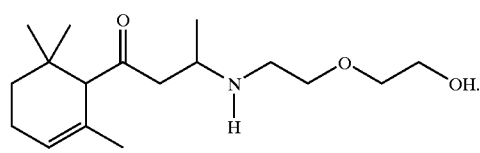

[21]Pro-fragrance which releases melonal, for example

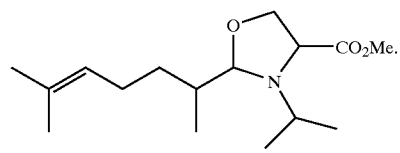

TABLE V-continued

|  | weight % | | |
|---|---|---|---|
| Ingredients | 2 | 3 | 4 |

[22]Pro-fragrance which releases triplal, for example

[23]Pro-fragrance which releases 9-decen-1-ol; for example

[24]Conventional fragrance accord.
[25]Minors include, inter alia, ethanol, 1,2-propanediol, methyl ethyl amine, sodium hydroxide, suds suppressers, dyes, perfumes, pro-perfumes, and opacifiers.

The enhanced duration fragrance delivery systems of the present invention are suitable for use in beauty care products. Non-limiting examples include, shampoos, conditioners, bath gels, skin creams, dipilitory, sunscreens, deodorants, antiperspirants, soaps, and the like.

In addition, articles of manufacture, inter alia, diapers, incontinence briefs, may make use of the delivery systems of the present invention.

What is claimed is:

1. A fragrance delivery system comprising:
   a) a pro-fragrance component comprising:
      i) P number of a pro-fragrance, a pro-accord, or mixtures thereof, each of which is capable of releasing at least one fragrance raw material f, wherein at least one of said fragrance raw materials, f, which is capable of being released, satisfies the boundary condition defined by:

$\chi > n(v_D)$ wherein $\chi$ is 100% of the amount of said fragrance raw material, f, which is releasable from all of said pro-fragrances or pro-accords which are capable of releasing said fragrance raw material; $v_D$ is the odor detection concentration of said one fragrance raw material, f, which satisfies said boundary condition; P is at least 1; n is a multiple of the odor detection concentration and is equal to at least 1;
      ii) optionally fragrance raw material release modifiers; and
   b) a free fragrance component comprising:
      i) an initial amount, $\epsilon$, of said at least one fragrance raw material, f, which satisfies the boundary condition defined in (a); wherein $\epsilon$ is defined as:

$\epsilon \leq a(\chi)$ a is 10;
      ii) optionally the balance one or more other fragrance raw materials, carriers, and adjunct ingredients.

2. A system according to claim 1 wherein at least 2 fragrance raw materials which are capable of being released by component (a) satisfy the boundary conditions:

$\chi > n(v_D)$ and are present in component (b) in an initial amount, $\epsilon$.

3. A system according to claim 1 wherein at least 3 fragrance raw materials which are capable of being released by component (a) satisfy the boundary conditions:

$\chi > n(v_D)$ and are present in component (b) in an initial amount, $\epsilon$.

4. A system according to claim 1 wherein at least 4 fragrance raw materials which are capable of being released by component (a) satisfy the boundary conditions:

$\chi > n(v_D)$ and are present in component (b) in an initial amount, $\epsilon$.

5. A system according to claim 1 wherein component (a) comprises 1 pro-fragrance.

6. A system according to claim 1 wherein component (a) comprises 1 pro-accord.

7. A system according to claim 1 wherein P is at least 3.

8. A system according to claim 1 wherein n is at least about 5.

9. A system according to claim 8 wherein n is at least about 25.

10. A system according to claim 9 wherein n is at least about 100.

11. A system according to claim 1 wherein a is 4.

12. A system according to claim 11 wherein a is 2.

13. A system according to claim 12 wherein a is 1.

14. A fragrance delivery system comprising:
   a) a pro-fragrance component comprising:
      i) P number of a pro-fragrance, a pro-accord, or mixtures thereof, which together release i number of fragrance raw materials, $f_i$, the index i identifies a particular fragrance raw material and the corresponding parameters, and at least a number j of said fragrance raw materials, $f_i$, satisfies the boundary condition defined by:

$$\chi_i > n(v_{Di})$$

wherein $\chi_i$ is 100% of the amount of the ith fragrance raw material, $f_i$, which is releasable from all of said pro-fragrances or pro-accords which are capable of releasing said ith fragrance raw material; $v_{Di}$ is the odor detection concentration of an ith fragrance raw material, whereby j number of said fragrance raw materials, $f_i$, satisfy said boundary condition; P is at least 1; i is at least 1; j is at least 1; n is a multiple of the odor detection concentration and is equal to at least 1;

ii) optionally fragrance raw material release modifiers; and b) a free fragrance component comprising:
i) an initial amount, $\epsilon_i$, of said j number of ith fragrance raw materials, $f_i$, which satisfy the boundary condition defined in (a); wherein $\epsilon_i$ of said ith fragrance raw material is defined as:

$$\epsilon_i \leq a(\chi_i)$$

a is 10;

ii) optionally the balance one or more other fragrance raw materials, carriers, and adjunct ingredients.

15. A system according to claim 14 wherein i is equal to 2.

16. A system according to claim 14 wherein i is equal to 3.

17. A system according to claim 14 wherein i is equal to 4.

18. A system according to claim 14 wherein i is less than or equal to 10.

19. A system according to claim 14 wherein j is 2.

20. A system according to claim 14 wherein j is 3.

21. A system according to claim 14 wherein j is 4.

22. A system according to claim 14 wherein P is at least 2.

23. A system according to claim 14 wherein for j equal to 1, n is at least about 5.

24. A system according to claim 14 wherein n is at least about 25.

25. A system according to claim 14 wherein for j equal to 1, n is at least about 100.

26. A system according to claim 14 wherein a is 4.

27. A system according to claim 26 wherein a is 2.

28. A system according to claim 27 wherein a is 1.

29. A fragrance delivery system comprising:
a) a pro-fragrance component comprising:
i) P number of a pro-fragrance, a pro-accord, or mixtures thereof, which together release i number of fragrance raw materials, $f_i$, the index i identifies a particular fragrance raw material and the corresponding parameters, and at least a number j of said fragrance raw materials, $f_i$, satisfies the boundary condition defined by:

$$\chi_i > n(v_{Di})$$

wherein $\chi_i$ is 100% of the amount of the ith fragrance raw material, $f_i$, which is releasable from all of said pro-fragrances or pro-accords which are capable of releasing said ith fragrance raw material; $v_{Di}$ is the odor detection concentration of an ith fragrance raw material, whereby j number of said fragrance raw materials, $f_i$, satisfy said boundary condition; P is at least 1; i is at least 1; j is at least 1; n is a multiple of the odor detection concentration and is equal to at least 1;

ii) optionally fragrance raw material release modifiers; and b) a free fragrance component comprising:
i) an initial amount, $\epsilon_i$, of said j number of ith fragrance raw materials, $f_i$, which satisfy the boundary condition defined in (a); wherein $\epsilon_i$ of said ith fragrance raw material is defined as:

$$(0.1)^a(\chi_i) \leq \epsilon_i$$

a is 5;

ii) optionally the balance one or more other fragrance raw materials, carriers, and adjunct ingredients.

30. A fragrance delivery system comprising:
a) a pro-fragrance component comprising:
i) P number of a pro-fragrance, a pro-accord, or mixtures thereof, which together release i number of fragrance raw materials, $f_i$, the index i identifies a particular fragrance raw material and the corresponding parameters, and at least a number j of said fragrance raw materials, $f_i$, satisfies the boundary condition defined by:

$$\chi_i > n(v_{Di})$$

wherein $\chi_i$ is 100% of the amount of the ith fragrance raw material, $f_i$, which is releasable from all of said pro-fragrances or pro-accords which are capable of releasing said ith fragrance raw material; $v_{Di}$ is the odor detection concentration of an ith fragrance raw material, whereby j number of said fragrance raw materials, $f_i$, satisfy said boundary condition; P is at least 1; i is at least 1; j is at least 1; n is a multiple of the odor detection concentration and is equal to at least 1;

ii) optionally fragrance raw material release modifiers; and b) a free fragrance component comprising:
i) an initial amount, $\epsilon_i$, of m number of said ith fragrance raw materials, $f_i$, which satisfy the boundary condition defined in (a); wherein $\epsilon_i$ of said ith fragrance raw material is defined as:

$$\log v_{Si} - \tfrac{1}{2}\log v_{Di} > \log \epsilon_i > \log v_{Si} + \tfrac{1}{2}\log v_{Di}$$

wherein $v_{Si}$ is the odor saturation concentration of said ith fragrance raw material; $v_{Di}$ is the odor detection concentration of said ith fragrance raw material; m is 1;

ii) optionally the balance one or more other fragrance raw materials, carriers, and adjunct ingredients.

31. A fragrance delivery system comprising:
a) a pro-fragrance component comprising:
i) P number of a pro-fragrance, a pro-accord, or mixtures thereof, each of which is capable of releasing at least one fragrance raw material f, wherein at least one of said fragrance raw materials, f, which is capable of being released, satisfies the boundary condition defined by:

$$\chi > n(v_D)$$

wherein $\chi$ is 100% of the amount of said fragrance raw material, f, which is releasable from all of said pro-fragrances or pro-accords which are capable of releasing said fragrance raw material; $v_D$ is the odor detection concentration of said one fragrance raw material, f, which satisfies said boundary condition; P is at least 1; n is a multiple of the odor detection concentration and is equal to at least 1; wherein at least one of said P number of pro-fragrances is a photo-labile pro-fragrance or pro-accord.
  ii) optionally fragrance raw material release modifiers; and
 b) a free fragrance component comprising:
  i) an initial amount, $\epsilon$, of said at least one fragrance raw material, f, which satisfies the boundary condition defined in (a); wherein $\epsilon$ is defined as:

$\epsilon \leq a(\chi)$ a is 10;
  ii) optionally the balance one or more other fragrance raw materials, carriers, and adjunct ingredients.

32. A composition having an enduring fragrance comprising:
 A) from about 0.001% by weight, of a fragrance delivery system comprising:
  a) a pro-perfume component comprising:
   i) P number of a pro-fragrance, a pro-accord, or mixtures thereof, which together release i number of fragrance raw materials, $f_i$, the index i identifies a particular fragrance raw material and the corresponding parameters, and at least a number j of said fragrance raw materials, $f_i$, satisfies the boundary condition defined by:

$\chi_i > n(v_{Di})$ wherein $\chi_i$ is 100% of the amount of the ith fragrance raw material, $f_i$, which is releasable from all of said pro-fragrances or pro-accords which are capable of releasing said ith fragrance raw material; $v_{Di}$ is the odor detection concentration of an ith fragrance raw material, whereby j number of said fragrance raw materials, $f_i$, satisfy said boundary condition; P is at least 1; i is at least 1; j is at least 1; n is a multiple of the odor detection concentration and is equal to at least 1;
   ii) optionally fragrance raw material release modifiers; and
  b) a free fragrance component comprising:
   i) an initial amount, $\epsilon_i$, of said j number of ith fragrance raw materials, $f_i$, which satisfy the boundary condition defined in (a); wherein $\epsilon_i$ of said ith fragrance raw material is defined as:

$\epsilon_i \leq a(\chi_i)$ a is 10;
   ii) optionally the balance one or more other fragrance raw materials, carriers, and adjunct ingredients; and
 B) the balance carriers and adjunct ingredients.

33. A composition comprising:
 A) from about 0.01% to about 75% by weight, of one or more active ingredients;
 B) from about 0.01% by weight, of a fragrance delivery system comprising:
  a) a pro-fragrance, P, which releases fragrance raw material, f, wherein P is present in an amount such that the releasable fragrance raw material concentration, $\chi$, is defined by the relationship:

$\chi > n(v_D)$ wherein $v_D$ is the odor detection concentration of the fragrance raw material, f, n is at least 1;
  b) said fragrance raw material, f, in an initial concentration amount, $\epsilon$, wherein $\epsilon$ is defined as:

$\epsilon \leq q$ wherein q is the weight percent of said active ingredient containing composition and equals 25; and
 C) the balance carriers and adjunct ingredients.

34. A process for delivering a sustained fragrance, said process comprising the steps of:
 a) selecting P number of a pro-fragrance, a pro-accord, or mixtures thereof, which together release i number of fragrance raw materials, $f_i$, wherein at least a number j of said fragrance raw materials, $f_i$, satisfies the boundary condition defined by:

$\chi_i > n(v_{Di})$ wherein $\chi_i$ is 100% of the amount of the ith fragrance raw material, $f_i$, which is releasable from all of said pro-fragrances or pro-accords which are capable of releasing said ith fragrance raw material; $v_{Di}$ is the odor detection concentration of said j number of fragrance raw materials, $f_i$, which satisfy said boundary condition; P is at least 1; j is at least 1; n is a multiple of the odor detection concentration and is equal to at least 1; and
 b) combining said P number of a pro-fragrance, a pro-accord, or mixtures thereof, with an initial amount, $\epsilon_i$, of said j number of ith fragrance raw materials, $f_i$, which satisfy the boundary condition defined in (a); wherein $\epsilon_i$ of said ith fragrance raw material is defined as:

$\epsilon_i \leq a(\chi_i)$ a is 10, to form a fragrance delivery system having a fragrance raw material releasing component and an initial fragrance raw material component.

* * * * *